(12) United States Patent
Mitsuhashi et al.

(10) Patent No.: US 6,251,247 B1
(45) Date of Patent: Jun. 26, 2001

(54) DETECTION OF DEGRADATION OF RNA USING MICROCHANNEL ELECTROPHORESIS

(75) Inventors: Masato Mitsuhashi; Mieko Ogura, both of Irvine, CA (US); Kenji Watanabe, Yuki; Yoichi Agata, Makabe-machi, both of (JP)

(73) Assignees: Hitachi Chemical Co., Ltd., Tokyo (JP); Hitachi Chemical Research Center, Inc., Irvince, CA (US)

( * ) Notice: Subject to any disclaimer, the term of this patent is extended or adjusted under 35 U.S.C. 154(b) by 0 days.

(21) Appl. No.: 09/281,385

(22) Filed: Mar. 30, 1999

Related U.S. Application Data
(60) Provisional application No. 60/080,277, filed on Apr. 1, 1998.

(51) Int. Cl.[7] .................. G01N 27/26; G01N 27/447
(52) U.S. Cl. .................. 204/451; 204/600; 204/601; 204/450
(58) Field of Search .................. 204/456, 451, 204/452, 453, 455, 466, 469, 601, 602, 603, 604, 605, 606, 616, 600, 450; 435/6; 536/25.4

(56) References Cited

U.S. PATENT DOCUMENTS

| | | | |
|---|---|---|---|
| 5,126,022 | 6/1992 | Soane et al. | 204/458 |
| 5,750,015 | 5/1998 | Soane et al. | 204/454 |
| 5,958,694 | * 9/1999 | Nikiforov | 435/6 |
| 6,071,745 | * 6/2000 | Lin et al. | 435/374 |

FOREIGN PATENT DOCUMENTS

| | | |
|---|---|---|
| 8-178897 | 7/1996 | (JP) . |
| WO 97/38300 | 10/1997 | (WO) . |

OTHER PUBLICATIONS

Michael Neumaier et al, "Fundamentals of Quality Assessment of Molecular Amplification Methods in Clinical Diagnostics" Clinical Chemistry, 44:1, pp. 12–26, 1998.*

Randy M. McCormick, et al., Microchemical Electrophoretic Separations of DNA in Injection–Molded Plastic Substrates, Analytical Chemistry, vol. 69, No. 14, Jul. 15, 1997.

* cited by examiner

*Primary Examiner*—Jill Warden
*Assistant Examiner*—John S. Starsiak, Jr.
(74) *Attorney, Agent, or Firm*—Kbobbe, Martens, Olson & Bear, LLP

(57) ABSTRACT

Degradation of RNA present in a sample is detected by using, as an indicator, rRNA included in the RNA. The steps include: (a) introducing the sample onto a microchannel, at an introducing point, filled with an electrophoresis separation gel; (b) conducting electrophoresis of rRNA fragments present in the sample to force rRNA fragments to migrate through the electrophoresis separation gel; (c) detecting rRNA fragments passing through a detection point located downstream of the introducing point, to obtain detection patterns; and (d) determining degradation of RNA present in the sample based on the detection patterns of rRNA. A sample containing degraded mRNA can also be screened by detecting rRNA degradation in the above microchannel electrophoresis.

14 Claims, 9 Drawing Sheets

DETECTION OF DEGRADATION OF RNA USING MICROCHANNEL ELECTROPHORESIS

This application claims the benefit of Provisional No. 60/080,277 filed Apr. 1, 1998.

BACKGROUND OF THE INVENTION

This invention relates to a method of detecting degradation of RNA, and particularly to that by separating and detecting rRNA in microchannel electrophoresis.

mRNA is widely used in biosciences for cDNA cloning, construction of expressed sequence tag (EST) databases, gene expression analysis, etc. In diagnostic molecular pathology, mRNA is also used frequently to detect or quantitate the levels of specific gene expression, such as bcr-ab1 translocation of Philadelphia chromosome in leukemia (Bortolin, et al., "Quantitative RT-PCR combined with time-resolved fluorometry for determination of BCR-ABL mRNA", Clin Chem 1996; 42:1924–9), point mutation of p53 gene in breast cancer (Lundeberg, et al., "Assessment of sequence-based p53 gene analysis in human breast cancer: messenger RNA in comparison with genomic DNA targets", Clin Chem 1998; 44:455–62), prostate-specific antigen transcript for micrometastasis of prostate cancer (Gala, et al., "Expression of prostate-specific antigen and prostate-specific membrane antigen transcripts in blood cells: Implications for the detection of hematogenous prostate cells and standardization", Clin Chem 1998; 44:472–81), etc. Many technologies and commercial kits are available for the purification of mRNA or total RNA from cells and tissues. However, the quality of mRNA is major concern among scientists because of its extreme instability against contaminated RNases. This is particularly important when the object is to isolate full-length DNA or to analyze gene expression, quantitatively as clinical diagnostics. The ratio of optical absorbency at 260 nm and 280 nm is the most common technique for the quality assessment of RNA. However, this provides information only as to whether or not proteins are contaminated in samples. Although Northern blot or reverse transcription-polymerase chain reaction (RT-PCR) is used to amplify housekeeping genes, the existence of PCR products of these genes in samples does not guarantee that RNA is entirely intact. An assay has been developed to determine the amount of total mRNA by capturing mRNA onto oligo(dT)-immobilized microplates followed by Yoyo-1-fluorescence measurement (Miura, et al., "Fluorometric determination of total mRNA with oligo(dT) immobilized on microtiter plates", Clin Chem 1996; 42:1758–64) or calorimetric detection of incorporated biotin-mononucleotides during cDNA synthesis on the microplate (Tominaga, et al., "Colorimetric ELISA measurement of specific mRNA on immobilized-oligonucleotide-coated microtiter plates by reverse transcription with biotinylated mononucleotides", Clin Chem 1996;42:1750–57). However, the quantity of mRNA does not mean that mRNA are free from degradation, because partially digested mRNA may be captured by oligo(dT). When purified mRNA is separated by agarose gel electrophoresis and stained with ethidium bromide, one can see the smear of mRNA. If the smear is distributed to a large molecular weight region, mRNA is considered to be of good quality. However, this assay is not quantitative. Therefore, there is no suitable procedure available for the analysis of the quality of mRNA.

Interestingly, a gold standard method exists for total RNA by agarose gel electrophoresis to identify 2–3 major bands, 28s, 18s, and 7S rRNA/(Neumaier, et al., "Fundamentals of quality assessment of molecular amplification methods in clinical diagnostics", Clin Chem 1998;44:12–26). If these bands disappear, RNA of the samples is considered as useless because RNA is digested by contaminated RNases during the purification procedure. Although agarose gel electrophoresis is easy to accomplish, one should take extra care against RNase contamination in an electrophoresis chamber, loading buffer, separation buffer, agarose gel, etc. Moreover, because of low sensitivity of ethidium bromide against RNA, a relatively large quantity of purified RNA is consumed by agarose gel electrophoresis. Thus, heretofore, no method is available to determine the quality of a sample containing RNA in a short time, with a very small quantity, without complication, and with high accuracy.

SUMMARY OF THE INVENTION

The present invention has, exploited a method of evaluating the occurrence of degradation of RNA in a sample. An objective of the present invention is to provide an easy-to-use, highly sensitive, rapid method of evaluating degradation of RNA in a sample.

Namely, one important aspect of the present invention is a method of detecting degradation of RNA present in a sample by using, as an indicator, rRNA included in the RNA, comprising the steps of: (a) introducing the sample onto a microchannel, at an introducing point, filled with an electrophoresis separation gel, said microchannel being a capillary channel having first and second ends to which voltage is applied separately; (b) conducting electrophoresis of rRNA fragments present in the sample by generating a voltage difference between the first and second ends of the microchannel to force rRNA fragments to migrate through the electrophoresis separation gel toward the second end; (c) detecting rRNA fragments passing through a detection point located downstream of the introducing point, to obtain detection patterns; and (d) determining degradation of RNA present in the sample based on the detection patterns of rRNA.

The method of the present invention allows very sensitive rRNA analysis, which requires only a small volume less than 1–3 $\mu$L. Further, the method is rapid (e.g., less than 3 min), reproducible, and easy-to-use. Surprisingly, no migration shift occurs in electrophoresis, thereby providing a reliable reading. The sensitivity in the method can be approximately 100-fold higher than that of conventional agarose gel electrophoresis. rRNA equivalent to $\frac{1}{10}$ to $\frac{1}{50}$ of a single cell can be subjected to this method. In view of a very low quantity of mRNA in cells, this method becomes extremely useful.

mRNA is a useful diagnostic indicator since the levels of specific gene expression can indicate certain disorders or sicknesses. In the present method, a sample containing degraded mRNA can be screened by detecting rRNA degradation in the above microchannel electrophoresis. Degradation of mRNA can be inferred from degradation of rRNA. Accordingly, the method is very useful at least as an initial quality control method for any of RNA-related experiments and diagnostics. In the above, degradation of rRNA is indicative of degradation of mRNA for the reasons below. Some RNase may be more active on mRNA than on rRNA, and complicated secondary structures of rRNA may prevent attack from RNases. Thus, if rRNA is not detected in the purified RNA samples, it is confirmed that the sample is useless for further analysis. Moreover, because the quantity of rRNA present in cells far exceeds that of mRNA, rRNA is a much more practical indicator than mRNA.

BRIEF DESCRIPTION OF THE DRAWINGS

FIG. 3A is a graph of relative fluorescence units (RFU) versus separation time (each number represents the size of fragments of HaeIII digests). FIG. 3B is a graph of size in log scale versus separation time in linear scale.

DETAILED DESCRIPTION OF THE PREFERRED EMBODIMENT

RNA Chip

A platform for microchannel electrophoresis in the present invention can be in any form. Microfabricated electrophoretic separation devices recently have become available (McCormick, et al., "Microchannel electrophoretic separations of DNA in injection-molded plastic substrates", Anal Chem 1997;69:2626–2630). Devices for microchannel electrophoresis are also disclosed in PCT International Publication No. WO 97/38300, U.S. Pat. No. 5,126,022 to Soane, et al., and U.S. Pat. No. 5,750,015 to Soane, et al. However, in the above publications, applications of the devices are restricted to DNA, a double-strand polynucleotide, for DNA sizing and DNA sequencing. This is mainly because DNA does not form a secondary structure and is very stable. In contrast, RNA is a single-strand polynucleotide and tends to form a secondary structure, and further, RNA is very prone to RNase. When RNA is subjected to electrophoresis, a migration shift normally is observed. Moreover, RNA is difficult to dye with ethidium bromide, for example. For the above reasons, one of ordinary skill in the art could not conceive the possibility or practicability of application of microchannel electrophoresis to RNA. In fact, no publication teaches application to RNA. In the present invention, the devices disclosed in the above publications can be used for the purpose of determination of degradation of RNA, especially mRNA.

Figure 1:
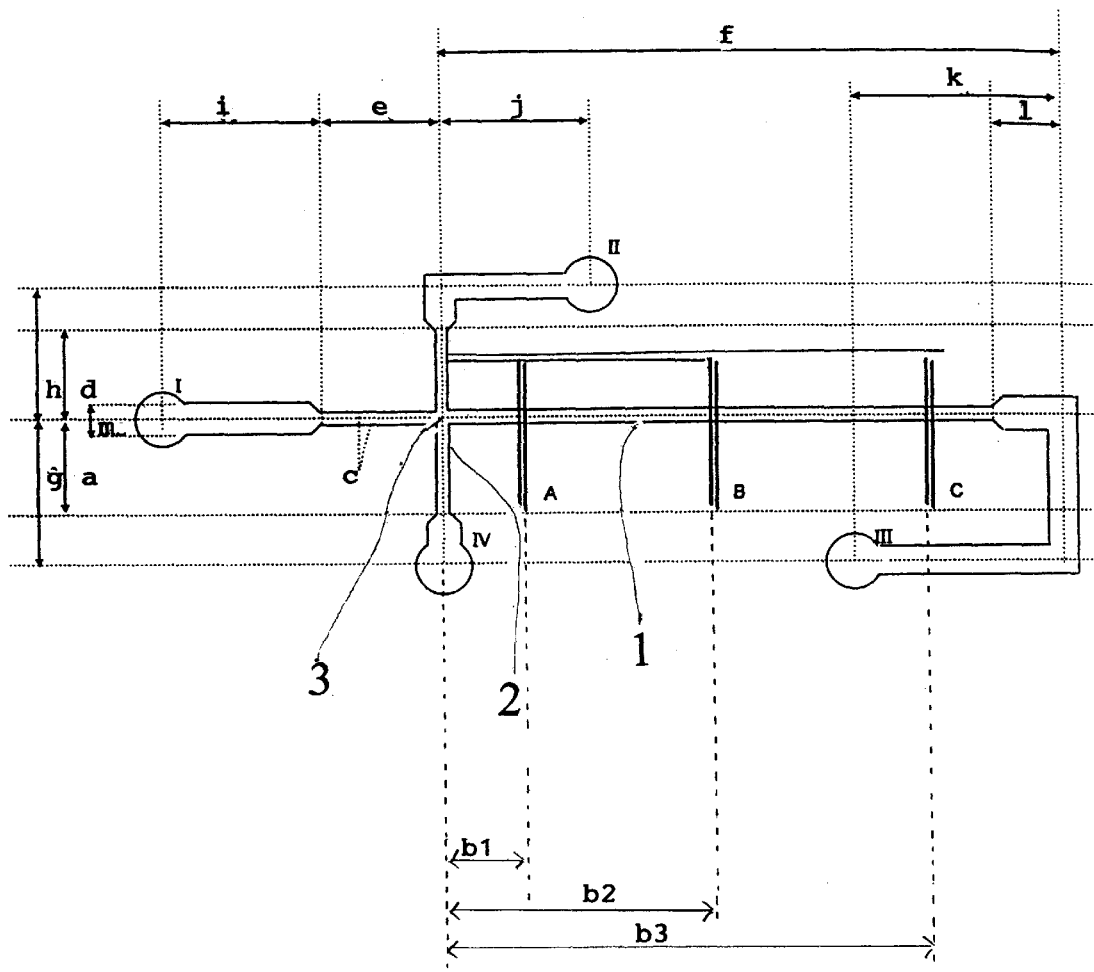
FIG. 1 is a schematic plane view illustrating an example of a configuration of microchannels.
Figure 2A:
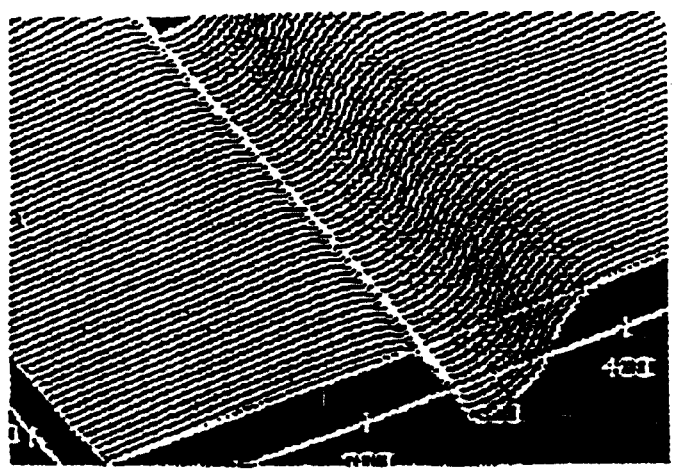
FIGS. 2A, 2B, and 2C are three-dimensional views of the structures of 3 different portions of microchannel (A, B, and C in FIG. 1, respectively) with a scanning electron microscope.
Figure 2B:
Figure 2C:
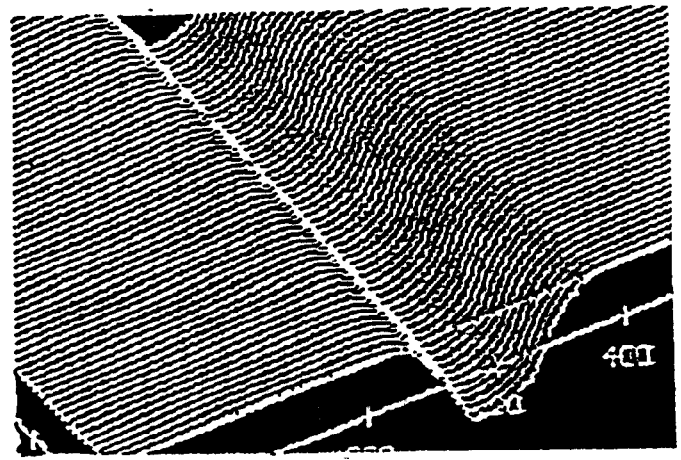

FIG. 1 is a schematic plane view illustrating an example of a configuration of microchannels of a plastic chip. In FIG. 1, I–IV indicate 4 independent reservoirs, and A–C are locations of physical examination. The depth of the injection channel (vertical, II–IV) and the separation channel (horizontal, I–III) is 40 $\mu$m, and a sample was applied to reservoir IV. Further, symbols "a" to "l" indicate length, and "a" is 1–5 mm (typically 2–4 mm), "b" (b1, b2, or b3) is 5–100 mm (typically 10–40 mm), "c" is 0.05–0.3 mm (typically 0.1–0.15 mm), "d" is 2–8 mm (typically 4 mm), "e" is 2–10 mm (typically 5 mm), "f" is 5–120 mm (typically 45 mm), "g" is 2–10 mm (typically, 6 mm), "h" is 2–10 mm (typically 6 mm), "i" is 3–15 mm (typically 10 mm), "j" is 3–15 mm (typically 10 mm), "k" is 5–25 mm (typically 15 mm), "l" is 1–6 mm (typically 3 mm), and "m" is 0.1–0.5 mm. In the above, large diameter portions represented by "g", "h", "i", "j", "k", and "m" can be omitted. Length a, i.e., the distance between the loading point and the crossing point, should be short enough to avoid separation of rRNA fragments to be detected (e.g., 18S and 28S) when crossing over the separation through the crossing point. That is, only one of them may go into the separation microchannel. Thus, preferably, the distance between the loading point and the crossing point is 1–5 mm. Length b, i.e., the distance between the introducing point and the detection point on the separation microchannel, should be such that rRNA fragments to be detected (e.g., 18S and 28S) are separated when passing through the detection point but are not overly attenuated to detect each rRNA fragment. While travelling on the separation microchannel from the crossing point toward the detection point, the fragments separately migrate depending on the molecule size; the smaller the molecule, the faster the fragment migrates. If length b is long, the distance between the fragments having different molecule sizes becomes significant (i.e., good resolution) whereas the concentration of each fragment passing through the detection point becomes low (i.e., poor detection intensity). Preferably, the distance between the introducing point and the detection point is 0.5–10 cm.

In the above, the chip is made of plastic such as acrylic resin by injection-molding, for example. However, the chip can be made of glass. Although the chip in the figure has a separation microchannel 1 and an injection microchannel 2 which intersect each other at a crossing point 3, the number of the microchannels can be one or more. In the case of two microchannels, the injection channel has two ends and is filled with the electrophoresis separation gel, wherein the sample is loaded onto the injection channel at a loading point and migrates through the injection channel toward the introducing point when a voltage difference is applied between the two ends of the injection channel, whereby the sample reaches the introducing point. If a single microchannel is used, the crossing point 3 is designated as a sample-introducing point. Reservoirs I–IV are provided with built-in electrodes. However, electrodes can be separately provided. Further, the size of the chip can vary as long as microchannel electrophoresis can be conducted. The separation microchannel may have a width of 10–200 $\mu$m, a depth of 10–100 $\mu$m, and a length of 30–100 mm.

The RNA chip can be mounted on a plexiglas electrophoresis stage and placed on a fluorescent microscope to detect migration of rRNA fragments. Fluorescent signals can be collected by a photometer, and digital data can be collected as previously described (McCormick, et al., Anal Chem 1997-69:2626–30).

Procedure of Microchannel Electrophoresis

In the invention, the method detects degradation of RNA present in a sample by using, as an indicator, rRNA included in the RNA. As described above, the method comprises the steps of: (a) introducing the sample onto a microchannel, at an introducing point, filled with an electrophoresis separation gel; (b) conducting electrophoresis of rRNA fragments present in the sample by generating a voltage difference between the first and second ends of the microchannel to force rRNA fragments to migrate through the electrophoresis separation gel toward the second end; (c) detecting rRNA fragments passing through a detection point located downstream of the introducing point, to obtain detection patterns; and (d) determining degradation of RNA present in the sample based on the detection patterns of rRNA.

In the above, the electrophoresis separation gel is a separation buffer containing a sieving polymer, e.g., a crosslinked polymer or a liner polymer, in an amount effective to conduct migration of rRNA. The liner polymer is preferred and includes an alkylcellolose derivative, for example, which is preferably selected from the group consisting of hydroxyethylcellulose, hydroxypropylmethylcellulose, hydroxypropylcellulose, and methylcellolose, in an amount of, e.g., 0.1–2% by weight in the gel. Without the sieving gel, rRNA does not migrate sufficiently for detection.

For example, the separation buffer comprises hydroxypropylmethylcellulose1 (HPMC), Tris buffer, boric acid, and ethidium bromide. The dye can be any florescence or U.V. dye which stains nucleic acids, such as YoPro-1™ (quinolinium,4-[(3-mehyl-2(3H)-benzoxazolylidene) methyl]-1-[3-(trimethylammonio)propyl]-,diiodide), Yoyo-1™ (quinolinium, 1,1'-[1,3-propanediylbis [(dimethylimino)-3,1-propanediyl]]bis[4-[)3-methyl-2-(3H)-benzoxazolylidene)methyl]]-,tetraiodie, PicoGreen™, and Sybergreen™. The dye can be included either in a sample or a separation buffer.

In FIG. 1, the separation buffer is loaded into reservoirs I, II, and III, and fills entire channels by means of both capillary action and vacuum action from the reservoir IV until all air bubbles are removed. RNA samples are then applied to reservoir IV. In order to apply the samples into the injection channel, electrophoresis is conducted by applying a voltage in such a way that (i) the sample migrates from reservoir IV to reservoir II, and (ii) after reaching the crossing point, the sample migrates toward reservoir III and passes through the detection point. For example, the levels of voltage applied may be in the following order: reservoir II>I>III/IV for step (i). For step (ii), the levels of voltage may be in the following order: reservoir III>II/IV>I. By viewing the crossing point of the injection channel and the separation channel with, e.g., a fluorescent microscope, it can be confirmed that the sample crosses the separation channel. The microscope is then moved to a detection point, 0.5–5 cm downstream of the crossing point of the injection and separation channels. Resolution can be improved if the distance between the crossing point and the detection point is long (e.g., 3–5 cm).

Two major components of rRNAs (e.g., 18S and 28S rRNA) can be separated on the plastic chip. The assay is rapid (less than 3 min), reproducible, RNase-free, disposable, easy-to-use and consumes only 1–2 µL of samples. More interestingly, the sensitivity of this chip-based assay is approximately 100-fold higher than that of conventional agarose gel electrophoresis. Because loaded samples actually used for electrophoresis can be as small as 0.1 nL, the detectable rRNA peaks can be derived from rRNA equivalent to 1/10 to 1/50 of a single cell. As shown in an example described below, the actual detection limit (e.g., Hae III digest) can be 10 ng/µL (I pg/0.I nL). These independent results (1/50 cell versus I pg) are consistent with each other and indicate usefulness because approximately 10 µg of total RNA are usually obtained from $10^6$ cells. Furthermore, the sensitivity of this assay can be improved further by replacing the mercury lamp with a high power laser, and switching ethidium bromide to more sensitive dyes, such as PicoGreen, YoPro-1, etc. Moreover, 1–2 µl, of samples may be applied on the chip, although approximately 0.1 nL of samples are consumed for separation. If one can handle nL quantity of liquid, this chip becomes extremely useful.

The present inventors have separated rRNA with conventional capillary electrophoresis (CEP) equipped with a laser (Beckman, Fullerton, Calif.). However, the electrophoresis on the chip exhibited significant advantages over CEP. First of all, the condition of the channels can be observed anywhere within the chip using a fluorescent microscope or even by the naked eye, which eases confirmation of electrophoresis and resolves many mechanical problems, such as bubbling, plugging, etc. Fluorescent signals are also observed during electrophoresis, and migration of samples to the right direction (in FIG. 1) is confirmed. The length of electrophoresis can be easily changed by moving the detection point anywhere within the channels. Because CEP reuses the same capillary over and over again, extensive washing steps are unavoidable between respective runs. That is problematic because the surface characteristics of the inner wall of the capillary may change after multiple washing processes, and may yield unreproducible results. It also requires time-consuming step(s) to exchange capillaries. More importantly, if RNase-rich sample is applied, one must take extra care to remove any contaminated RNases from capillaries. These problems can be entirely eliminated by using disposable chips.

Recently, microfabricated chip-based electrophoresis was reported from some laboratories (Woolley, et al., "Ultra-high-speed DNA fragment separations using microfabricated capillary array electrophoresis chips", Proc Natl Acad Sci USA 1994;91:11348–52; Woolley, et al., "Ultra-high-speed DNA sequencing using capillary electrophoresis chips", Anal Chem 1995-67:3676–80; Schmalzing, et al., "DNA typing in thirty seconds with a microfabricated device", Proc Natl Acad Sci USA 1997;94:10273–8). However, these chips have utilized glass or silica as substrates which are not suitable for mass production. The application was also limited to DNA In contrast to DNA applications, rRNA separation does not require high resolution, and allows the use of channels of, e.g., 100 Em in width. Narrow channels produce many technical problems. The RNA chip may be made by injection-molded technology, similar to that of McCormick et. al. (McCormick, et al., Anal Chem 1997-69:2626–30), which is capable of producing large quantities of disposable chips. Appropriate acrylic substrates can be selected to minimize autofluorescence. Further, during manufacturing processes, thin plastic films are automatically adhered on the surface of the chip to cover injection and separation channels. This process makes the chip RNase-free. Therefore, microchannel electrophoresis on plastic chip as described in this study is ideal for rRNA analysis.

EXAMPLES

Materials

Cell culture media and appropriate antibiotics, fetal calf serum (FCS), DNA marker φx 174 Hae III (Gibco-BRL, Gaithersburg, Md.), λ Hind II (Promega, Madison, Wis.), U937 cells (American Type Culture Collection, Rockville, Md.) were purchased from designated suppliers. All other chemicals were purchased from Sigma (St. Louis, NU). Plastic chips for microchannel electrophoresis (RNA chip) were manufactured at Goshomiya Works, Hitachi Chemical (Shimodate, Japan) (FIG. 1). RNA sample preparation U937 cells were grown in RPMI 1640 containing 100 U/mL penicillin, 100 µg/mL streptomycin, and 100 mL/L FCS at 37° C. in CO2:air, 5:95 (by vol), and were subcultured 2–3 times a week, as previously described (Miura, et al., Clin Chem 1996; 42:1758–64). Viability was always >90%, as assessed by the exclusion of trypan blue. The number of cells was determined with a hemocytometer. Fresh lung tissues were collected from rats, and immediately processed for RNA preparation. Samples were mixed with caotropic buffer (Toyobo, Osaka, Japan), and applied to automatic RNA extractor (MFX-2000, Toyobo). RNA was bound to silica beads followed by removal of unbound materials by magnet separation, according to the manufacturer's protocol.

RNA Chip

FIG. 1 is a schematic plane view illustrating the configuration of microchannels of the plastic chip. In FIG. 1, each number represents the length in mm, I–IV indicate 4 independent reservoirs, and A–C are locations of physical examination. The depth, of the injection channel (vertical, II–IV) and the separation channel (horizontal, I–III) is 40 µm, and a sample was applied to reservoir IV.

In order to analyze the surface characteristics of themicrochannels, the RNA chip was loaded into a vacuum chamber, and the structures of 3 different portions of microchannel were analyzed by three-dimensional scanning electron microscope (ERA-8000, Elionix, Tokyo, Japan) (Taguchi, "Measurement of microtopography: 3D measuring method by SEM", Jpn J Tribology 1990; 351–7).

Equipment of microchannel electrophoresis

The RNA chips were mounted on a plexiglas electrophoresis stage (Soane Biosciences, Hayward, Calif.), and placed on a fluorescent microscope (Microphot-FXA, Nikon, Tokyo, Japan) equipped with 20X CF Plan ELWD objective lens (Technical Instrument, San Francisco, Calif.), 546/10 nm excitation filter, 580 nm dichroic mirror, 590 in G-IB emission filter (Nikon), and 100 W mercury lamp (Model HB 10101AF). Fluorescent signals were collected by a photometer (D104B, Proton Technology International, Squth Brunswick, N.J.), and digital data were collected (DT 2837 A/D and DT2815 D/A board, Data translation, Marlboro, Mass.), as previously described (McCormick, et al., "Microchannel electrophoretic separations of DNA in injection-molded plastic substrates", Anal Chem 1997-69:2626–30). A high voltage power supply was purchased from Soane Biosciences.

Procedure of Microchannel Electrophoresis

A separation buffer consisting of 0.4% hydroxypropylmethylcellulose1 (HPMC), 44.75 mM Tris, 44.75 mM boric acid, pH8.0, and 5 µg/mL ethidium bromide was loaded into reservoirs I, II, and III, and filled entire channels by means of both capillary action and vacuum action from the reservoir IV until all air bubbles were removed. The RNA samples were then applied to reservoir IV. In order to apply the samples into the injection channel (the vertical channel in FIG. 1), electrophoresis was conducted with voltage of +100 V, +300 V, 0 V, and 0 V at reservoir I, II, III, and IV, respectively. By viewing the crossing point of the injection channel and the separation channel (horizontal channel in FIG. 1) with a fluorescent microscope, it is confirmed that the samples crossed the separation channel. The microscope was then moved to a detection point 0.5–5 cm downstream of the crossing point of the injection and separation channels. Electrophoretic separation was begun by applying voltage of 0 V, +500 V, +1000 V and +500 V at reservoirs I, II, III, IV, respectively.

Preliminary Example 1: Separation Profile of Small Fragments of DNA

In the microchannel electrophoresis procedure described above, three µL of DNA marker (HaeIII digest of φx174, 40 µg/ml) was applied (in place of the RNA sample) to reservoir IV. The microscope was set 5 cm downstream from the cross section between injection and separation channels. Mercury lamp (100 W) was used to excite ethidium bromide-DNA complex, and fluorescence of 590 mm (relative fluorescence units, RFU) was collected.

Figure 3A:
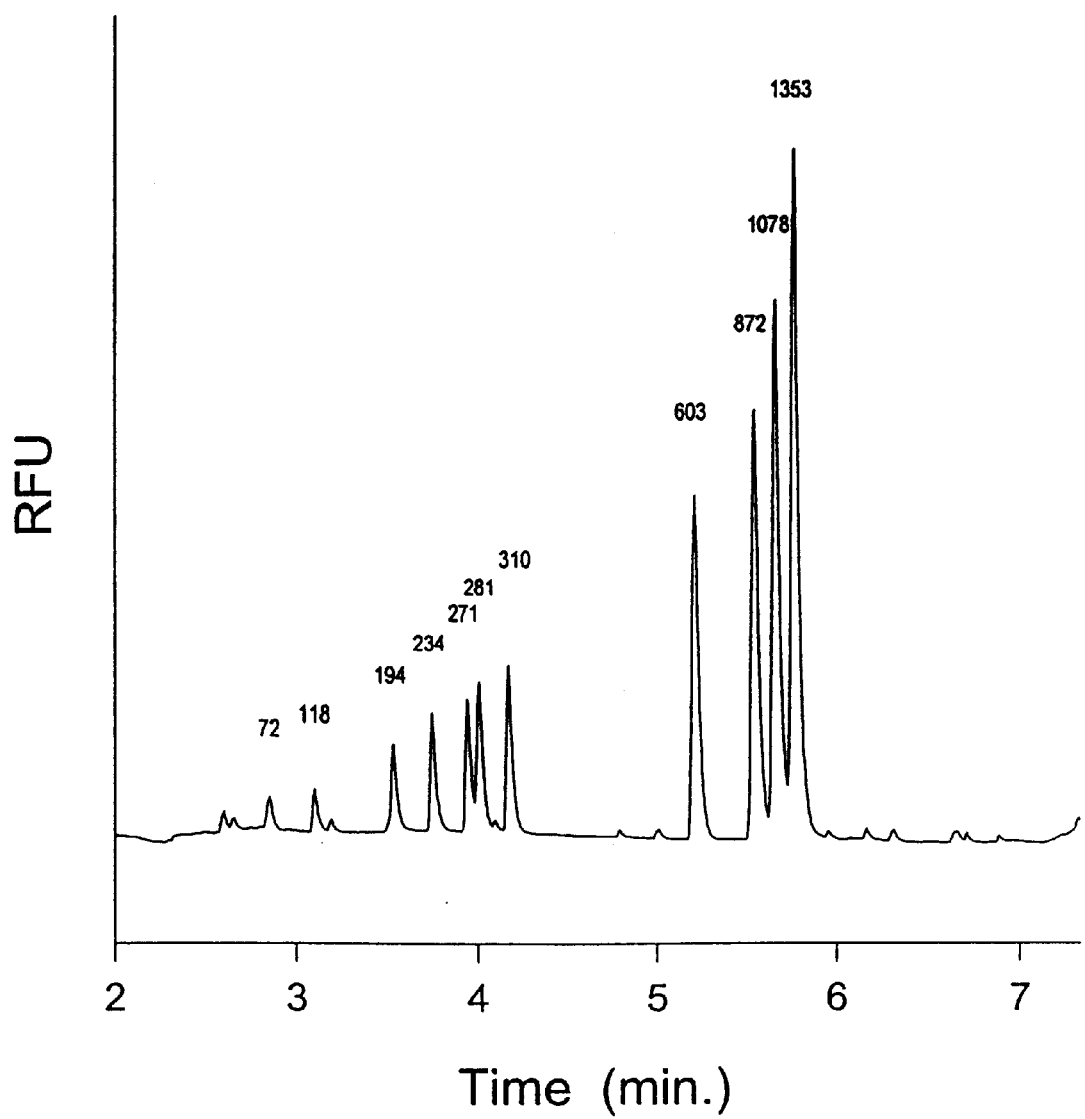
FIGS. 3A and 3B are graphs showing electrophoretic separation of DNA marker (φx1.74 HaeIII) through a separation microchannel on a microchip.
Figure 3B:
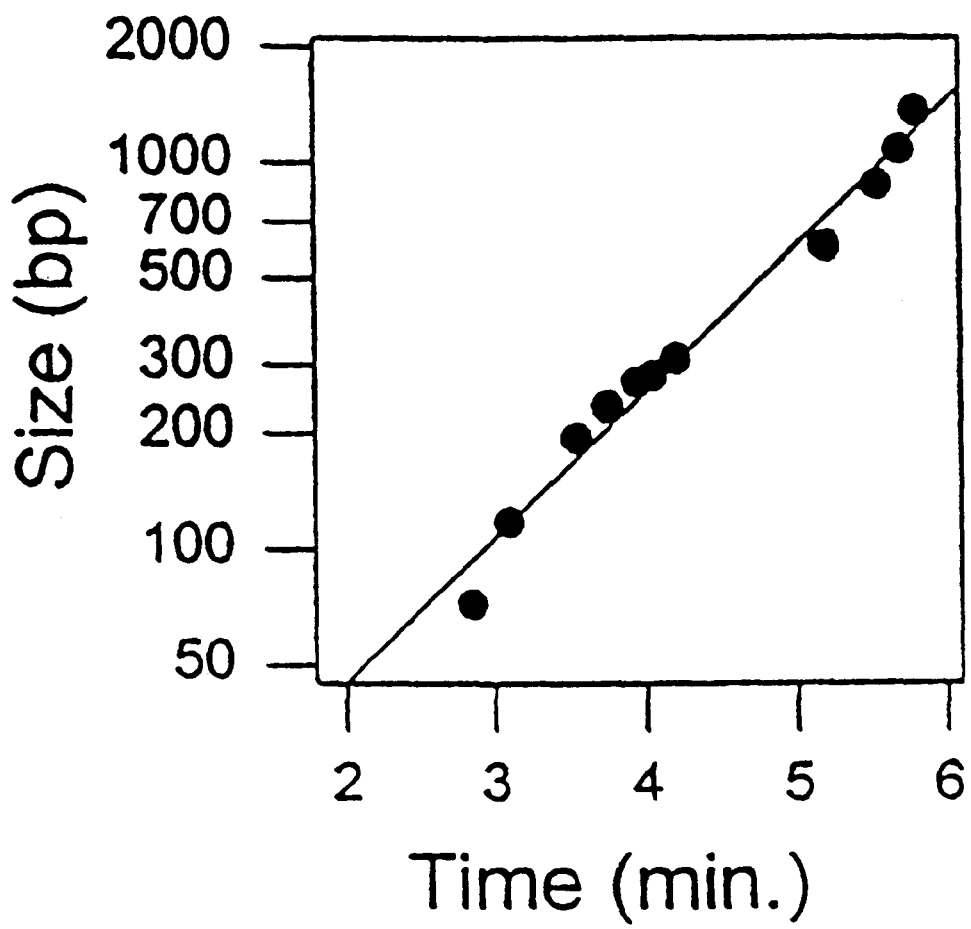

As shown in FIGS. 3A and 3B, the all DNA fragments from 72 bp to 1353 bp were clearly separated with a linear correlation between size (in log scale) and separation time (in linear scale) (see FIG. 3B). Moreover, the fluorescent intensity of larger fragments was always higher than that of small fragments. This is reasonable because each fragment exists in the same molar ratio, and large DNA fragments react with more ethidium bromide. Another emphasis is the separation of 271 and 281 bp fragments, suggesting that the chip provides at least 10 bp resolution under these conditions. In order to determine the detection sensitivity, the same DNA marker of different concentrations of the DNA marker (A: 1 µg/µL, B: 100 ng/µL, C: 10 ng/µL, and D: 1 ng/µL) was applied to the microchip and electrophoresis was conducted as described above and in FIG. 3. A detection point was set 4 cm downstream of the crossing point of the injection and separation channels.

Figure 4:
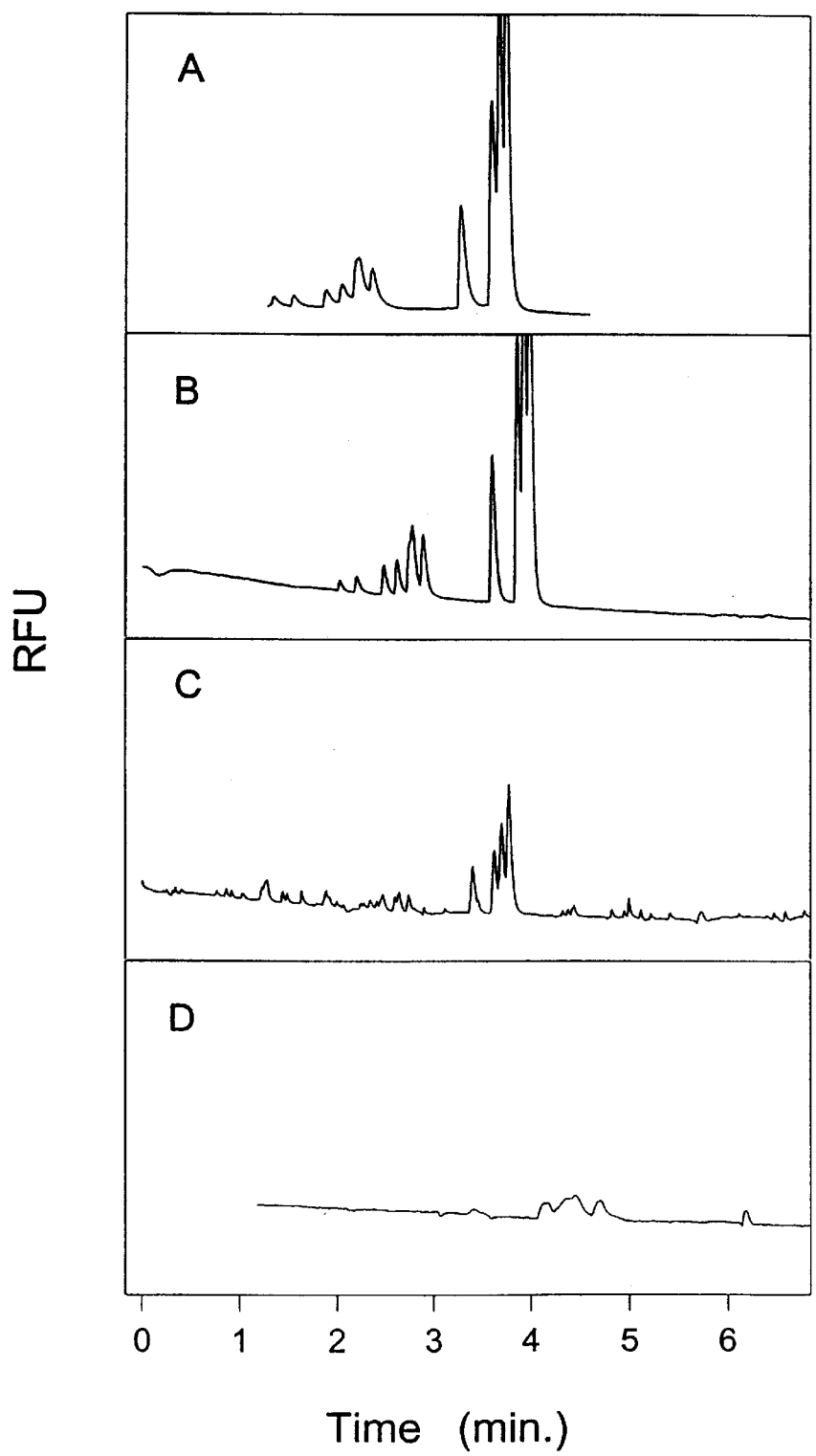
FIG. 4 is a graph of relative fluorescence units (RFU) versus separation time, showing dose dependency of DNA marker on microchannel electrophoresis.

FIG. 4 is a graph of relative fluorescence units (RFU) versus separation time, showing dose dependency of DNA marker on microchannel electrophoresis (A: 1 µg/µL, B: 100 ng/µL, C: 10 ng/µL, and D: 1 ng/µL). As shown in FIG. 4, fluorescent signals as low as 0.01 µg/µL of fragments having molecular weights higher than 603 bp were detected.

Preliminary Example 2: Conventional Agarose Gel Electrophoresis

The RNA samples were mixed with loading buffer (0.25% bromophenol blue, 0.25% xylene cyanol FF, I mmol/L EDTA, 40% sucrose in diethylpyrocarbonate-treated water), and applied to 1.0% agarose gel, which was dissolved in 1xTBE. Electrophoresis was conducted in IxTBE buffer containing 0.1 µg/mL ethidium bromide, at a constant voltage of 100 V for approximately 30 min.

Figure 5A:
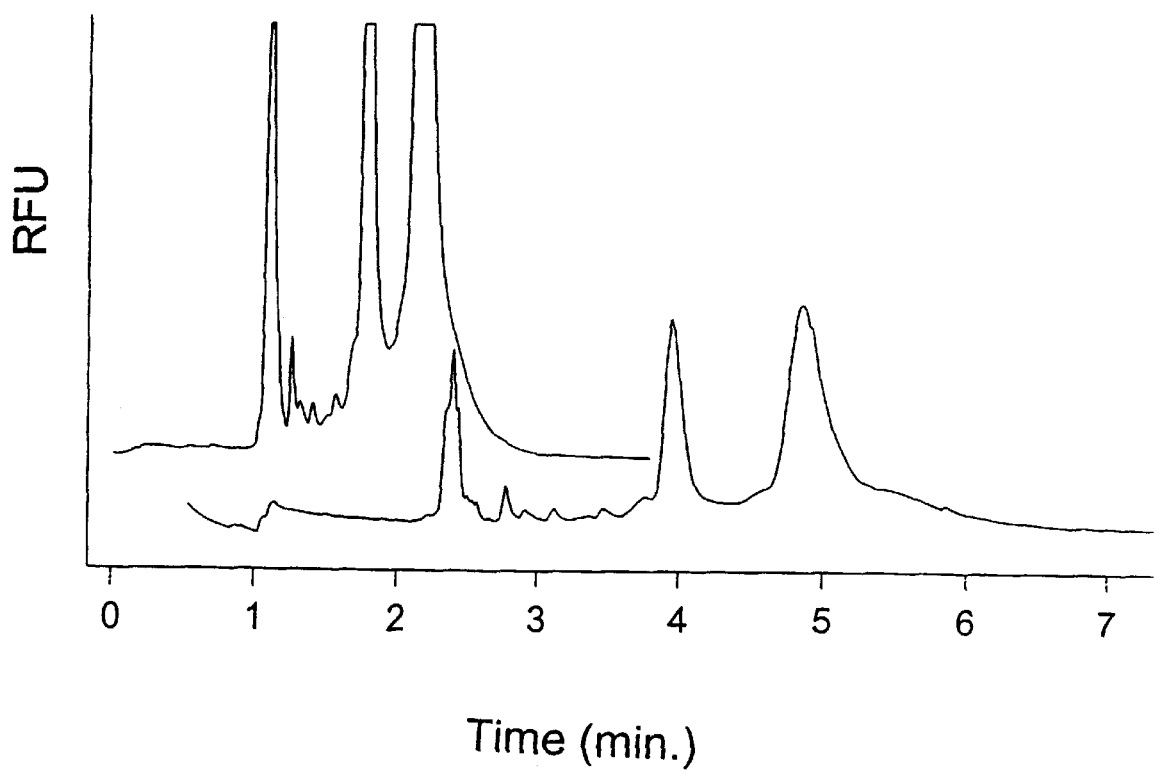
FIGS. 5A and 5B show microchannel electrophoresis of total RNA extracted from rat lung, using microchips A (FIG. 5A) and B (FIG. 5B), wherein fluorescent signals were detected at 1 cm (FIG. 5A: upper trace, FIG. 5B: all 3 traces) or 4 cm (FIG. 5A: lower trace) from the crossing point of the injection and separation channels.
Figure 5B:
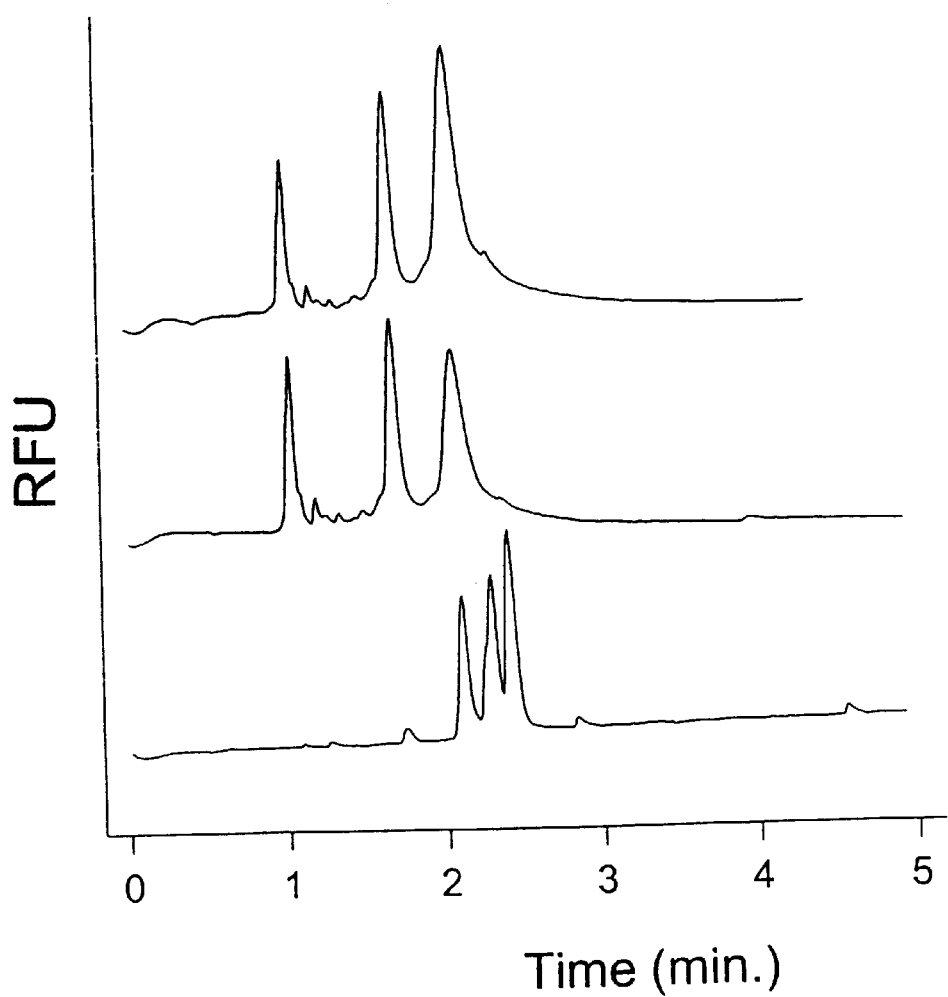
Figure 5C:
FIG. 5C shows agarose gel electrophoresis of an RNA and DNA marker (Hind III).

In general, RNA is separated by denaturing gel electrophoresis to prevent complicated secondary structure (Sambrook, et al., "Extraction, purification and analysis of messenger RNA from eukaryotic cells", In: Molecular cloning, a laboratory manual, 2nd ed. Cold Spring Harbor, N.Y.: Cold Spring Harbor Laboratory Press, 1989;7.1–7.87; Skeidsvoll, et al., "Analysis of RNA by capillary electrophoresis", Electrophoresis 1996;17:1512–7). However, two rRNA bands were clearly and reproducibly identified in conventional agarose gel electrophoresis (FIG. 5C).

Example 1: Separation Profile of RNA Using RNA Chip

RNA was separated in the chip with 0.4% HPMC as sieving polymer without any denaturing agent. FIGS. 5A and 5B show microchannel electrophoresis of total RNA extracted from rat lung. RNA (4 µg/mL) was purified from fresh rat lung as described above, and applied to 2 different microchips (A and B) for electrophoresis. Fluorescent signals were detected at 1 cm (A: upper trace, B: all 3 traces) or 4 cm (A: lower trace) from the crossing point of the injection and separation channels. DNA marker, λ Hind II (50 μg/mL) was also analyzed in the same chip (B). Both the RNA and the DNA marker were analyzed by 1% agarose gel electrophoresis and stained with ethidium bromide (FIG. 5C).

As shown in FIGS. 5A and 5B, both 28S and 18S RNA were separated in the chip even with a separation length as short as 1 cm (FIG. 5A, upper trace), although a longer separation channel (4 cm) exhibited better resolution (FIG. 5A, lower trace). Small RNA fragments containing 7S rRNA, 4–5S tRNA, and possible RNA fragments migrated earlier than 18S rRNA and formed additional peak(s). RNAs were not separated without using sieving polymers, and optimal concentrations of HPMC was 0.4% (data not shown). In order to determine the size of each peak, X Hind III marker was also separated in the same chip. As shown in lower trace of FIG. 5B, the largest RNA peak migrated at a spot similar to that for 2,027–2,322 bp, suggesting the peak was 28s rRNA. Interestingly, the second largest peak (probable 18s rRNA) migrated at a spot similar to that for 564 bp, whereas in agarose gel electrophoresis this RNA was larger than 564 bp. The 18S rRNA may migrate differently between the agarose gel and the liner gel.

The separation pattern of these 3 peaks (28S, 18S, and small fragments) were reproducible when the samples were repeatedly applied to the same chip (Intra-assay) (FIG. 5B). The chip-to-chip variation was also negligible (FIGS. 5A and 5B). In addition, various RNA samples derived from different tissues and cultured cells were analyzed. The results were always consistent with and equivalent to that of conventional agarose gel electrophoresis (data not shown). When RNA was prepared from RNase-rich pancreas, small intestine, granulocytes, etc., rRNA was detected neither with the chip nor by agarose gel electrophoresis (data not shown).

Figure 6:
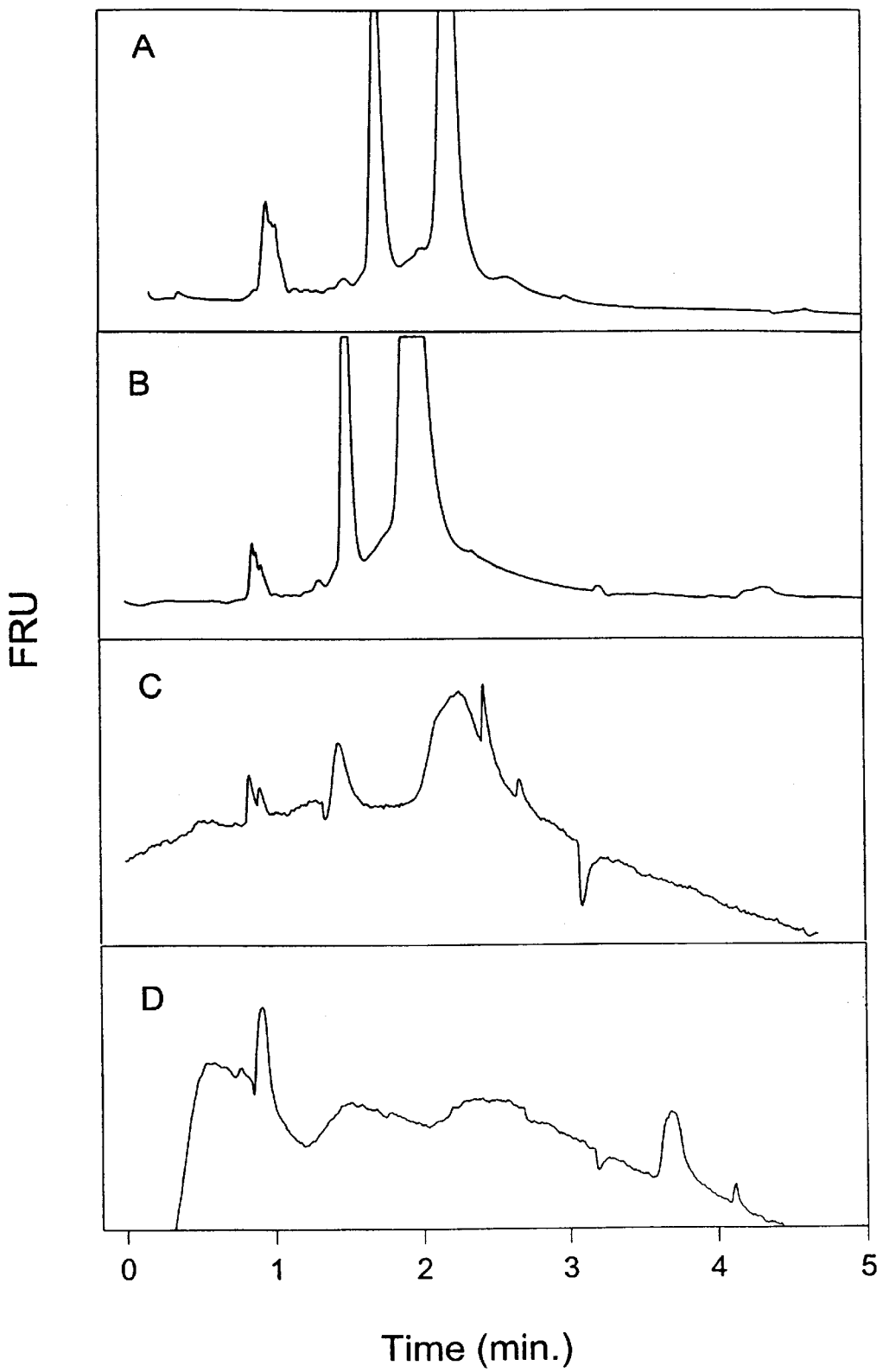
FIG. 6 is a graph of relative fluorescence units (RFU) versus separation time, showing dose dependency of RNA on microchannel electrophoresis (A: equivalent to $10^4$ cells/$\mu$L, B: $10^3$ cells/$\mu$L C: $10^2$ cells/$\mu$L, and D: 10 cells/$\mu$L).

The RNA samples were then diluted and applied to the chip to determine the detection limit of this assay. FIG. 6 is a graph of relative fluorescence units (RFU) versus separation time, showing dose dependency of RNA on microchannel electrophoresis (A: equivalent to $10^4$ cells/μL, B: $10^3$ cells/EL C: $10^2$ cells/μL, and D: 10 cells/μL). As shown in FIG. 6, surprisingly, the fluorescent signals of rRNA were detected from an RNA solution equivalent to 200 cells/μL. In parallel experiments, these diluted samples were also analyzed by agarose gel electrophoresis. Using conventional settings of an ultraviolet illuminator and ethidium bromide stains, rRNA bands were visible from samples equivalent to 20,000 cells/μL (data not shown). Actual injection volume of each separation was approximately 0.1 nL (0.0001 mm$^3$ at the crossing point of the injection and separation channels), suggesting that each rRNA peak was derived from less than 1/10 of rRNA in a single cell (FIG. 6).

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of detecting degradation of RNA present in a sample by using, as an indicator, rRNA included in the RNA, comprising the steps of:

loading the sample onto an injection channel at a loading point located downstream of a crossing point where the injection channel and a microchannel meet, said injection channel and said microchannel being plastic capillary channels having a width of approximately 100–200 μm filled with an electrophoresis separation gel, said injection channel having an unbranched straight portion extending from the loading point to the crossing point, said microchannel having an unbranched straight portion extending from the crossing point to a detection point located between the crossing point and a distal end of the microchannel;

generating a first voltage gradient between the loading point and a distal end of the injection channel until rRNA fragments present in the sample are forced to migrate through the electrophoresis separation gel and reach the crossing point;

when the rRNA fragments reach the crossing point, generating a second voltage gradient between the crossing point and the distal end of the microchannel, said second voltage gradient being greater than said first voltage gradient, thereby conducting electrophoresis of the rRNA fragments;

detecting rRNA fragments passing through the detection point located downstream of the crossing point, to obtain detection patterns; and determining degradation of RNA present in the sample based on the detection patterns of rRNA.

2. A method according to claim 1, wherein the electrophoresis separation gel is a separation buffer containing a liner polymer in an amount effective to conduct migration of rRNA.

3. A method according to claim 2, wherein the liner polymer is an alkylcellolose derivative.

4. A method according to claim 3, wherein the alkylcellolose derivative is selected from the group consisting of hydroxyethylcellulose, hydroxypropylmethylcellulose, hydroxypropylcellulose, and methylcellolose.

5. A method according to claim 4, wherein the alkylcellolose derivative is hydroxypropylmethylcellulose and is contained in an amount of 0.1–2% by weight in the gel.

6. A method according to claim 1, wherein the distance between the loading point and the crossing point on the injection channel is short enough to avoid separation of 18S and 28S rRNA fragments, if any, in the sample when crossing over the microchannel at the crossing point.

7. A method according to claim 6, wherein the distance between the loading point and the crossing point is 1–5 mm.

8. A method according to claim 7, wherein the distance between the introducing point and the detection point is 0.5–10 cm.

9. A method according to claim 7, wherein the distance between the introducing point and the detection point on the microchannel is such that 18S and 28S rRNA fragments, if any, in the sample are separated when passing through the detection point but are not overly attenuated to detect each rRNA fragment.

10. A method according to claim 1, wherein the sample or the electrophoresis separation gel comprises a fluorescent or ultraviolet dye which stains nucleic acids.

11. A method according to claim 1, wherein the sample comprises rRNA and mRNA, and the degradation of RNA is regarded as degradation of mRNA.

12. A method according to claim 1, wherein the sample contains total RNA extracted from cells.

13. A method according to claim 12, wherein the sample contains total RNA extracted from 100–600 cells per μL of the sample.

14. A method of screening a sample containing mRNA and rRNA, said mRNA being degraded, comprising the steps of:

loading the sample onto an injection channel at a loading point located downstream of a crossing point where the injection channel and a microchannel meet, said injection channel and said microchannel being plastic capillary channels having a width of approximately 100–200 µm filled with an electrophoresis separation gel, said injection channel having an unbranched straight portion extending from the loading point to the crossing point, said microchannel having an unbranched straight portion extending from the crossing point to a detection point located between the crossing point and a distal end of the microchannel;

generating a first voltage gradient between the loading point and a distal end of the injection channel until rRNA fragments present in the sample are forced to migrate through the electrophoresis separation gel and reach the crossing point;

when the rRNA fragments reach the crossing point, generating a second voltage gradient between the crossing point and the distal end of the microchannel, said second voltage gradient being greater than said first voltage gradient, thereby conducting electrophoresis of the rRNA fragments;

detecting rRNA fragments passing through the detection point located downstream of the crossing point, to obtain detection patterns;

determining degradation of RNA present in the sample based on the detection patterns of rRNA; and screening the sample if degradation of mRNA is determined.

* * * * *